(12) United States Patent
Sauer

(10) Patent No.: US 11,490,989 B2
(45) Date of Patent: Nov. 8, 2022

(54) SURGICAL PROCEDURE KIT

(71) Applicant: LSI Solutions, Inc., Victor, NY (US)

(72) Inventor: Jude S Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 17/386,860

(22) Filed: Jul. 28, 2021

(65) Prior Publication Data

US 2021/0353382 A1    Nov. 18, 2021

Related U.S. Application Data

(62) Division of application No. 15/983,063, filed on May 17, 2018, now Pat. No. 11,103,327.

(60) Provisional application No. 62/507,734, filed on May 17, 2017.

(51) Int. Cl.
| | |
|---|---|
| *A61B 90/50* | (2016.01) |
| *A61B 50/33* | (2016.01) |
| *A61B 50/22* | (2016.01) |
| *A47F 5/10* | (2006.01) |
| *A47B 43/00* | (2006.01) |

(52) U.S. Cl.
CPC .............. *A61B 90/50* (2016.02); *A61B 50/22* (2016.02); *A61B 50/33* (2016.02); *A47B 43/00* (2013.01); *A47F 5/10* (2013.01)

(58) Field of Classification Search
CPC ........... A61B 50/20; A61B 5/24; A61B 90/50; A61B 50/33; A61B 50/22; A47F 5/105; A47F 5/11; A47F 5/112; A47F 5/114; A47F 5/10; A47B 23/043; A47B 23/044; A47B 97/08; A47B 43/00; B65D 5/504
See application file for complete search history.

(56) References Cited

U.S. PATENT DOCUMENTS

| | | | | |
|---|---|---|---|---|
| 1,117,824 A | | 11/1914 | Fleming | |
| 1,411,022 A | * | 3/1922 | Heidenreich | G09F 1/04 248/459 |
| 1,546,983 A | * | 7/1925 | House | B65D 73/0085 211/74 |
| 1,614,977 A | * | 1/1927 | Ausmus | B42F 13/402 D19/91 |
| 1,684,124 A | * | 9/1928 | Burgess | B65D 73/0042 248/152 |
| 1,705,116 A | * | 3/1929 | Howland | G09D 3/02 40/120 |
| 1,718,406 A | * | 6/1929 | Bruce | G09F 5/00 211/73 |

(Continued)

*Primary Examiner* — Devin K Barnett
(74) *Attorney, Agent, or Firm* — Michael E. Coyne

(57) ABSTRACT

A surgical procedure kit includes a base, a first expansion panel having a first edge pivotably coupled to a first edge of the base, a first tent panel having a first edge pivotably coupled to a second edge of the first expansion panel, a second expansion panel having a first edge pivotably coupled to a second edge of the first tent panel and a second tent panel having a first edge pivotably coupled to the second edge of the second expansion panel. The base, the first tent panel, and the second tent panel each includes a receptacle configured to releasably hold a surgical device. In addition, the base, the first expansion panel, the first tent panel, the second expansion panel and the second tent panel are configurable between a deployed state and a shipping state.

20 Claims, 9 Drawing Sheets

(56) References Cited

U.S. PATENT DOCUMENTS

| | | | | | |
|---|---|---|---|---|---|
| 1,845,952 A * | 2/1932 | Wright | B42F 13/402 |
| | | | D19/78 |
| 1,897,143 A * | 2/1933 | Powell | B65D 83/0847 |
| | | | 229/175 |
| 1,997,310 A * | 4/1935 | Roege | G09F 5/00 |
| | | | 211/72 |
| 2,012,551 A * | 8/1935 | Steen | A47B 23/043 |
| | | | 248/463 |
| 2,076,683 A * | 4/1937 | Tharp | G09F 5/02 |
| | | | 206/214 |
| 2,091,260 A * | 8/1937 | Farkas | G09F 1/00 |
| | | | 283/56 |
| 2,110,429 A * | 3/1938 | Sunderhauf | A47F 5/112 |
| | | | 248/459 |
| 2,229,427 A * | 1/1941 | Tanner | A47F 5/112 |
| | | | 206/45.3 |
| 2,252,571 A * | 8/1941 | Kohn | A47G 1/141 |
| | | | 248/459 |
| 2,255,492 A * | 9/1941 | Peters | B65D 83/0005 |
| | | | 53/461 |
| 2,282,280 A * | 5/1942 | Yogg | G09F 1/04 |
| | | | 40/124.15 |
| 2,288,739 A * | 7/1942 | Peters | B65D 5/16 |
| | | | 229/149 |
| 2,302,677 A * | 11/1942 | Crane | B65D 71/0051 |
| | | | 206/170 |
| 2,324,194 A * | 7/1943 | Campiglia | A61F 17/00 |
| | | | D3/217 |
| 2,334,997 A * | 11/1943 | Doll | B65D 83/0847 |
| | | | 229/175 |
| 2,361,562 A * | 10/1944 | Park | B42D 15/00 |
| | | | 229/92.1 |
| 2,407,592 A * | 9/1946 | Wathen | G09F 1/065 |
| | | | 229/92.5 |
| 2,431,835 A * | 12/1947 | Smith | G09F 1/04 |
| | | | 40/124.15 |
| 2,444,987 A * | 7/1948 | Giessen | B65D 5/2042 |
| | | | 206/499 |
| 2,453,908 A * | 11/1948 | Harhay | B65D 71/0051 |
| | | | 229/117.14 |
| 2,483,464 A * | 10/1949 | Johnson | B65D 5/727 |
| | | | 206/499 |
| 2,490,356 A * | 12/1949 | Hummel | A47B 23/043 |
| | | | 248/463 |
| 2,637,924 A * | 5/1953 | Hutt | G09F 1/065 |
| | | | 40/539 |
| 2,652,647 A * | 9/1953 | Suciu | G09F 15/00 |
| | | | 248/459 |
| 2,726,835 A * | 12/1955 | Hummel | A47F 5/112 |
| | | | 248/459 |
| 2,784,929 A * | 3/1957 | Diening | A47B 23/043 |
| | | | 248/463 |
| 2,806,603 A * | 9/1957 | Van Der Molen | B04B 7/18 |
| | | | 210/380.1 |
| 2,881,662 A * | 4/1959 | Harris | B60Q 7/005 |
| | | | 229/87.01 |
| 2,975,905 A * | 3/1961 | Foland | G09F 21/22 |
| | | | 248/459 |
| 3,013,656 A * | 12/1961 | Murphy, Jr. | A61B 50/36 |
| | | | 206/370 |
| 3,099,398 A * | 7/1963 | Croteau | B25H 3/02 |
| | | | 439/577 |
| 3,174,244 A * | 3/1965 | Walton | B42D 15/047 |
| | | | 40/124.15 |
| 3,195,255 A * | 7/1965 | Toulmin, Jr. | G03B 21/00 |
| | | | 116/63 P |
| 3,199,765 A * | 8/1965 | Locke | B65D 5/02 |
| | | | 229/93 |
| 3,234,676 A * | 2/1966 | Colicki | G09F 1/04 |
| | | | 40/748 |
| 3,263,820 A * | 8/1966 | McFadden | A61M 5/008 |
| | | | 211/70.1 |
| 3,278,020 A * | 10/1966 | Murphy | A47F 7/00 |
| | | | 206/481 |
| 3,294,229 A * | 12/1966 | McConnell | B65D 75/54 |
| | | | 24/563 |
| 3,362,609 A * | 1/1968 | Freedy | B65D 5/504 |
| | | | 493/356 |
| 3,381,928 A * | 5/1968 | White | A47B 23/043 |
| | | | 248/455 |
| 3,428,235 A * | 2/1969 | Randazzo | B65D 71/36 |
| | | | 206/427 |
| 3,430,841 A * | 3/1969 | Kanaga | B65D 31/18 |
| | | | 383/125 |
| 3,462,020 A * | 8/1969 | Hall | A47F 5/112 |
| | | | 206/419 |
| 3,493,104 A * | 2/1970 | Tempelhof | B65D 5/008 |
| | | | 229/162.1 |
| 3,501,018 A * | 3/1970 | Solo | B44B 1/00 |
| | | | 211/163 |
| 3,516,538 A * | 6/1970 | Antwerpen | B65D 85/48 |
| | | | 206/453 |
| 3,575,285 A * | 4/1971 | Kahn | B65D 73/00 |
| | | | 40/124.06 |
| 3,718,261 A * | 2/1973 | Woofter | B43M 99/008 |
| | | | 248/152 |
| 3,751,172 A * | 8/1973 | Seitz | B01L 9/06 |
| | | | 356/244 |
| 4,064,797 A * | 12/1977 | Forlani | A47J 37/06 |
| | | | 99/341 |
| 4,068,760 A * | 1/1978 | Johnson, Jr. | A45D 24/38 |
| | | | 206/564 |
| 4,105,182 A * | 8/1978 | Jacobson | A47B 23/044 |
| | | | 248/459 |
| D251,082 S * | 2/1979 | Petrie | D3/247 |
| 4,181,220 A * | 1/1980 | Zicko | B65D 5/5035 |
| | | | 206/443 |
| 4,213,520 A * | 7/1980 | Sarna | A45C 9/00 |
| | | | 248/444.1 |
| 4,237,097 A * | 12/1980 | McDuffie | A47G 33/00 |
| | | | 422/126 |
| 4,258,847 A * | 3/1981 | Nierman | B65D 21/0202 |
| | | | 220/23.6 |
| 4,288,935 A * | 9/1981 | Cross | G09D 3/04 |
| | | | 40/120 |
| 4,384,647 A * | 5/1983 | Schweizer | B42F 17/18 |
| | | | 206/214 |
| 4,429,793 A * | 2/1984 | Ehmann | A61M 5/003 |
| | | | 62/457.2 |
| 4,433,780 A * | 2/1984 | Ellis | B42D 15/022 |
| | | | 229/921 |
| 4,478,332 A * | 10/1984 | Wiestmiller | A61B 50/37 |
| | | | 206/370 |
| 4,526,414 A * | 7/1985 | Jones | A01K 97/06 |
| | | | 294/146 |
| 4,544,123 A * | 10/1985 | Peacock | A47B 19/08 |
| | | | 206/45.24 |
| 4,573,576 A * | 3/1986 | Krol | A61J 15/0034 |
| | | | 206/471 |
| 4,607,817 A * | 8/1986 | Aquino | A47B 23/044 |
| | | | 206/214 |
| 4,709,895 A * | 12/1987 | Mardak | A47B 23/044 |
| | | | 248/459 |
| 4,765,462 A * | 8/1988 | Rose, Jr. | G11B 33/0494 |
| | | | D19/27 |
| 4,798,747 A * | 1/1989 | Laramee | E01F 9/654 |
| | | | 229/116 |
| 4,813,902 A * | 3/1989 | Messer | B42D 15/02 |
| | | | 40/539 |
| 4,896,820 A * | 1/1990 | Harrington | B65D 81/3453 |
| | | | 229/117.03 |
| 4,917,240 A * | 4/1990 | Roberts | B65D 85/52 |
| | | | 47/41.12 |
| 4,927,073 A * | 5/1990 | Esposito | B65D 5/48026 |
| | | | 229/120.31 |
| 5,010,669 A * | 4/1991 | Moran | G09F 1/08 |
| | | | 229/92.8 |

(56) References Cited

U.S. PATENT DOCUMENTS

| | | | | |
|---|---|---|---|---|
| 5,080,316 A * | 1/1992 | MacEwan | A47B 23/044 | 248/459 |
| 5,107,985 A * | 4/1992 | Bezrutczyk | B65D 5/0254 | 206/757 |
| 5,127,519 A * | 7/1992 | Tsao | A47G 23/0616 | 229/117.14 |
| 5,144,942 A * | 9/1992 | Decane | A61B 1/00144 | 606/1 |
| 5,251,935 A * | 10/1993 | Bottiglieri | B42F 13/402 | 402/73 |
| 5,267,652 A * | 12/1993 | Carroll | B26D 7/01 | 410/32 |
| 5,367,127 A * | 11/1994 | Dormon | H02G 1/00 | 206/443 |
| 5,409,282 A * | 4/1995 | Bale | A45C 3/00 | 294/146 |
| 5,411,141 A * | 5/1995 | Bounds | A47G 21/14 | 248/37.3 |
| 5,417,341 A * | 5/1995 | Petriekis | B65D 75/38 | 220/592.25 |
| 5,613,311 A * | 3/1997 | Burtch | G09F 1/06 | 40/539 |
| D386,939 S * | 12/1997 | Kelly | D7/359 | |
| 5,779,053 A * | 7/1998 | Partika | A61B 50/33 | 206/370 |
| 5,813,415 A * | 9/1998 | Slali | A45D 29/20 | 132/73 |
| 5,819,448 A * | 10/1998 | Kieves | G09F 21/06 | 40/124.06 |
| 5,839,590 A * | 11/1998 | Weiner | B65D 5/008 | 229/116 |
| 5,848,693 A * | 12/1998 | Davis | A61B 50/33 | 206/370 |
| 5,855,351 A * | 1/1999 | Cziraky | A47B 97/04 | 248/460 |
| 5,884,783 A * | 3/1999 | Proulx | B65D 81/36 | 211/70.1 |
| 5,884,889 A * | 3/1999 | Crosby | A47B 23/044 | 248/444 |
| 5,915,556 A * | 6/1999 | Simpson | B65D 81/05 | 206/521 |
| 5,915,564 A * | 6/1999 | Hsi-Chang | B65D 73/0085 | 206/784 |
| 5,927,672 A * | 7/1999 | Ruff | G09F 1/14 | 248/452 |
| 6,000,542 A * | 12/1999 | Smith | A47G 27/0487 | 206/349 |
| 6,056,120 A * | 5/2000 | Hollingsworth | A47F 7/0028 | 211/70.1 |
| 6,065,659 A * | 5/2000 | Faz | A45C 11/26 | 224/684 |
| 6,090,073 A * | 7/2000 | Gill | A61M 25/04 | 604/164.01 |
| 6,102,568 A * | 8/2000 | Davis | B65D 33/02 | 229/117.34 |
| 6,113,867 A * | 9/2000 | Mayer | A61L 2/26 | 206/370 |
| 6,269,961 B1 * | 8/2001 | Porcelli | A47F 5/112 | 211/73 |
| 6,270,049 B1 * | 8/2001 | Olvey | A47B 96/202 | 248/447 |
| 6,273,274 B1 * | 8/2001 | Lyles | A47F 7/06 | 211/32 |
| 6,273,278 B1 * | 8/2001 | Enyedy | A47F 7/0071 | 211/85.4 |
| 6,349,491 B1 * | 2/2002 | Able | G09F 1/10 | 40/124.06 |
| 6,382,412 B1 * | 5/2002 | Wood | B65D 5/422 | 248/152 |
| D459,220 S * | 6/2002 | Clark | D9/415 | |
| 6,418,648 B1 * | 7/2002 | Hollingsworth | G09F 1/04 | 40/124.14 |
| 6,427,371 B2 * | 8/2002 | Olson | A47G 1/141 | 40/124.14 |
| D487,551 S * | 3/2004 | Lee | D6/582 | |
| 6,935,133 B2 * | 8/2005 | Keeter | A61M 5/003 | 62/457.2 |
| 6,959,814 B1 * | 11/2005 | Hyman | A61M 5/003 | 62/457.2 |
| 7,025,381 B2 * | 4/2006 | Lockhart | B42F 11/00 | 402/73 |
| 7,111,733 B1 * | 9/2006 | Foote | A45C 15/00 | 383/38 |
| 7,182,305 B2 * | 2/2007 | Dempsey | A47F 7/14 | 248/455 |
| 7,225,573 B2 * | 6/2007 | Shaffer | G09F 1/06 | 40/661.09 |
| 7,284,347 B2 * | 10/2007 | Rodrigues | G09F 3/20 | 40/737 |
| 7,334,768 B1 * | 2/2008 | Lum | A47B 23/04 | 248/444 |
| 7,410,053 B2 * | 8/2008 | Bowen | B25H 3/06 | 206/370 |
| 7,527,235 B2 * | 5/2009 | Hummel | G09F 1/06 | 248/454 |
| 7,694,932 B1 * | 4/2010 | Ngan | B42D 5/043 | 40/107 |
| 7,735,644 B2 * | 6/2010 | Sirichai | A45F 5/02 | 206/45.24 |
| 7,814,821 B2 * | 10/2010 | Chenel | B65D 71/0029 | 206/139 |
| 8,114,105 B2 * | 2/2012 | Sauer | A61B 10/04 | 604/22 |
| 8,123,189 B2 * | 2/2012 | Phifer | A47B 23/044 | 190/30 |
| 8,181,786 B1 * | 5/2012 | Alas | B65D 77/003 | 206/570 |
| D667,831 S * | 9/2012 | Stravitz | D14/447 | |
| 8,282,065 B1 * | 10/2012 | Stone | A47B 23/044 | 16/221 |
| 8,313,496 B2 * | 11/2012 | Sauer | A61B 1/00071 | 606/139 |
| D679,278 S * | 4/2013 | Cho | D14/440 | |
| 8,459,190 B2 * | 6/2013 | Erdie | B65D 5/0254 | 108/51.3 |
| D689,501 S * | 9/2013 | Fong | D14/447 | |
| 8,679,065 B2 * | 3/2014 | Schuman | G09F 3/205 | 248/459 |
| 8,757,399 B2 * | 6/2014 | Wolfbauer | A47F 7/0028 | 211/60.1 |
| D720,454 S * | 12/2014 | Sauer | D24/145 | |
| 8,911,677 B2 * | 12/2014 | Gerstner | A61B 50/30 | 206/370 |
| 8,925,722 B2 * | 1/2015 | Poon | A45C 11/00 | 206/45.24 |
| 8,926,640 B2 * | 1/2015 | Sauer | A61B 17/0483 | 606/144 |
| 8,950,720 B1 * | 2/2015 | Carr | F16M 11/38 | 248/460 |
| 9,027,768 B2 * | 5/2015 | Hagadorn | A47B 49/004 | 211/163 |
| 9,898,938 B1 * | 2/2018 | Perrin | B42D 15/042 | |
| 9,995,428 B2 * | 6/2018 | Schwartz | A47B 23/04 | |
| D823,854 S * | 7/2018 | Enqvist | D14/440 | |
| 10,105,126 B2 * | 10/2018 | Sauer | A61B 17/29 | |
| 10,125,915 B1 * | 11/2018 | Phifer | A47B 23/002 | |
| D863,066 S * | 10/2019 | Fraser | D9/721 | |
| 2002/0190110 A1 * | 12/2002 | Polloni | B65D 85/1048 | 206/268 |
| 2003/0038047 A1 * | 2/2003 | Sleva | A61B 50/31 | 206/370 |
| 2003/0042214 A1 * | 3/2003 | Virvo | A47F 7/00 | 211/163 |
| 2003/0121811 A1 * | 7/2003 | Roshdy | A61B 50/30 | 206/363 |
| 2003/0136036 A1 * | 7/2003 | Zubli | G09F 1/04 | 40/124.15 |

(56) References Cited

U.S. PATENT DOCUMENTS

| | | | |
|---|---|---|---|
| 2003/0155259 A1* | 8/2003 | Koseki | A61B 17/06133 206/363 |
| 2004/0065571 A1* | 4/2004 | Gammons | A61L 2/26 206/363 |
| 2004/0187368 A1* | 9/2004 | Foster | G09F 1/04 40/124.06 |
| 2006/0076302 A1* | 4/2006 | Pretorius | A47K 1/09 211/72 |
| 2007/0158234 A1* | 7/2007 | Sakai | B65D 5/0254 206/784 |
| 2007/0221811 A1* | 9/2007 | Hauser | A47B 23/043 248/454 |
| 2007/0289184 A1* | 12/2007 | Cheng | B42D 15/045 40/124.06 |
| 2008/0093254 A1* | 4/2008 | Girgis | A61J 7/04 206/535 |
| 2008/0127536 A1* | 6/2008 | Carter | G09F 1/00 40/124.14 |
| 2008/0229632 A1* | 9/2008 | Dieden | G09F 1/14 40/124.06 |
| 2008/0236000 A1* | 10/2008 | Bostick | G09F 1/06 40/124.14 |
| 2009/0205996 A1* | 8/2009 | Celis | A45F 5/00 206/570 |
| 2010/0059560 A1* | 3/2010 | Lanum | A61B 50/31 224/257 |
| 2010/0072265 A1* | 3/2010 | Holloway | B65D 5/4279 229/115 |
| 2010/0300926 A1* | 12/2010 | Specker | B65D 5/504 206/587 |
| 2011/0016757 A1* | 1/2011 | Beckett | B42D 15/045 83/13 |
| 2011/0056412 A1* | 3/2011 | Grammer | A45C 9/00 108/1 |
| 2011/0297147 A1* | 12/2011 | Lick | A61B 50/31 128/202.16 |
| 2012/0037523 A1* | 2/2012 | Diebel | A45C 13/005 206/320 |
| 2012/0138766 A1* | 6/2012 | Chen | F16M 11/041 248/456 |
| 2012/0175408 A1* | 7/2012 | Wang | B65D 5/4275 229/115 |
| 2012/0248048 A1* | 10/2012 | Wu | F16M 11/10 211/26 |
| 2012/0273448 A1* | 11/2012 | Hsu | F16M 11/10 211/195 |
| 2012/0285055 A1* | 11/2012 | Glass | B42F 7/145 40/124.06 |
| 2013/0036635 A1* | 2/2013 | Mayer | G09F 9/30 40/124.06 |
| 2013/0062245 A1* | 3/2013 | Folchini | A61M 5/002 493/162 |
| 2013/0220850 A1* | 8/2013 | Wingate, III | A45C 11/00 206/223 |
| 2014/0215869 A1* | 8/2014 | Emoff | G09F 1/04 40/124.14 |
| 2015/0030742 A1* | 1/2015 | Jameson | A47J 37/0694 426/523 |
| 2015/0257515 A1* | 9/2015 | Bernard | F16M 11/28 211/33 |

* cited by examiner

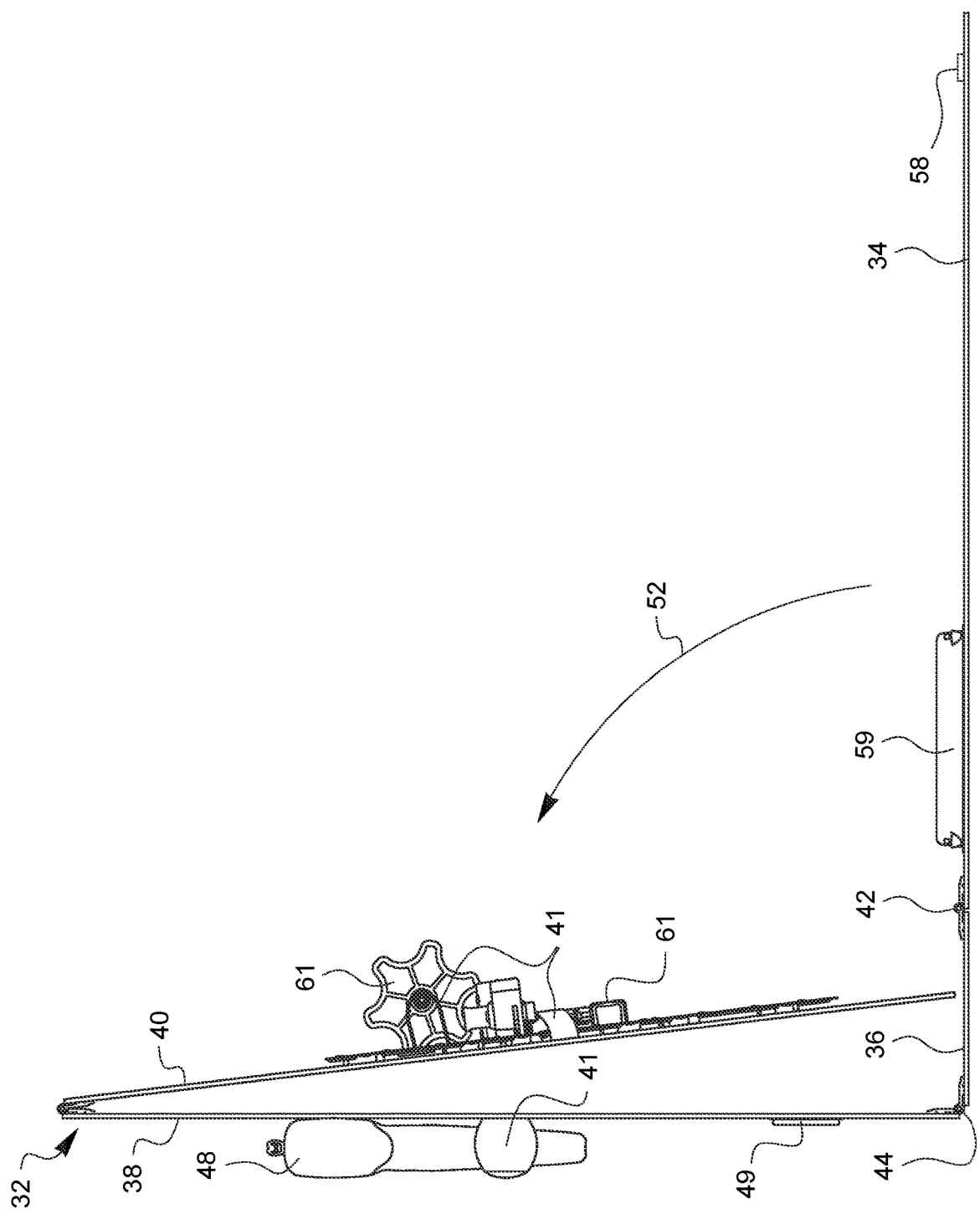

SURGICAL PROCEDURE KIT

RELATED APPLICATIONS

This application is a divisional of U.S. application Ser. No. 15/983,063, filed May 17, 2018 and entitled "SURGICAL PROCEDURE KIT," which claims priority to U.S. Provisional Patent Application No. 62/507,734, filed May 17, 2017 and entitled "SURGICAL PROCEDURE KIT," each of which is hereby incorporated by reference in its entirety.

FIELD

The claimed invention relates to packaging for surgical devices, and more specifically to surgical procedure kit.

BACKGROUND

Laparoscopic, endoscopic, and other types of minimally invasive surgical procedures often rely on percutaneous introduction of surgical instruments into an internal region of a patient where the surgical procedure is to be performed. Such procedures provide immense benefits to patients, including less perioperative pain, shorter hospital stays, and a quicker return to normal life and activities. In order to enable these benefits, however, a wide variety and large number of specialized surgical instruments are often needed for particular minimally invasive surgical procedures. For example, for a minimally invasive cardiac valve replacement procedure, the contemplated surgical instruments might include a rib retractor, aortic retractors, various cannulas, multiple types and quantities of automated suturing devices, suture, suture loaders for the automated suturing devices, suture snares, a scope holder, suture management devices, automated mechanical knotting devices, mechanical knots, and suturing devices for use with replacement heart valves. While all of these different items could be, and often are, packaged separately, the amount of packaging necessary to accommodate all of these items approaches a wasteful level. Furthermore, even if all of these items are lumped into a single package using traditional packaging techniques, the devices, when set on many operating room tables take up more space than is available on the table. Therefore, it would be advantageous to have a surgical procedure kit which utilized a compact packaging design that enables packing of multiple surgical devices into a single package while enabling all the items in the kit to be accessed easily from an operating room table without having to first remove the items from the kit and without having to sift through packing layers.

SUMMARY

A surgical procedure kit is disclosed. The surgical procedure kit includes a base, an expansion panel, a first tent panel, and a second tent panel.

Other features of the surgical procedure kit may include one or more of the following features, such as a first edge of the base which is pivotably coupled to a first edge of the expansion panel; a second edge of the expansion panel which is pivotably coupled to a first edge of the first tent panel; and a second edge of the first tent panel which is pivotably coupled to a first edge of the second tent panel. The surgical procedure kit may also include features where the base includes one or more stops in the proximity of a second edge of the base, these stops configured to receive a second edge of the second tent panel. The surgical procedure kit may also include a second expansion panel. The surgical procedure kit may include at least one receptacle configured to releasably hold at least one surgical device on each of the base, the first tent panel, the second tent panel, and either or both of the expansion panels.

The surgical procedure kit may also be configured into a shipping state for packaging and shipping, and a deployed position or deployed state during operation and use during surgical procedures.

BRIEF DESCRIPTION OF DRAWINGS

FIG. 4 is a side view showing an intermediate deployment position of the surgical procedure kit of FIG. 3, with the first and second tent panels rotated away from the base.

DETAILED DESCRIPTION

Figure 1:
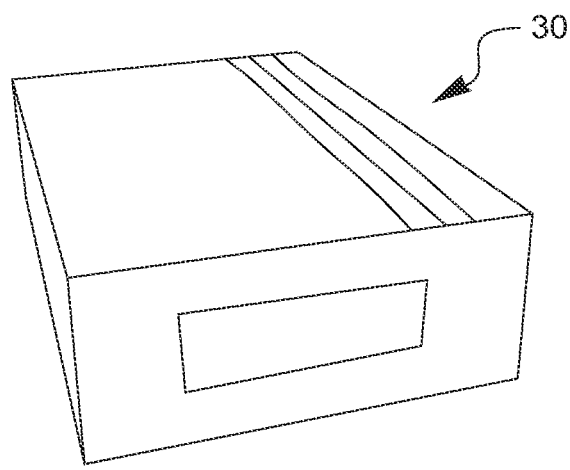
FIG. 1 is a perspective view of a sealed box housing an embodiment of a surgical procedure kit.

FIG. 1 illustrates a perspective view of a sealed box 30 which houses an embodiment of a surgical procedure kit.

Figure 2:
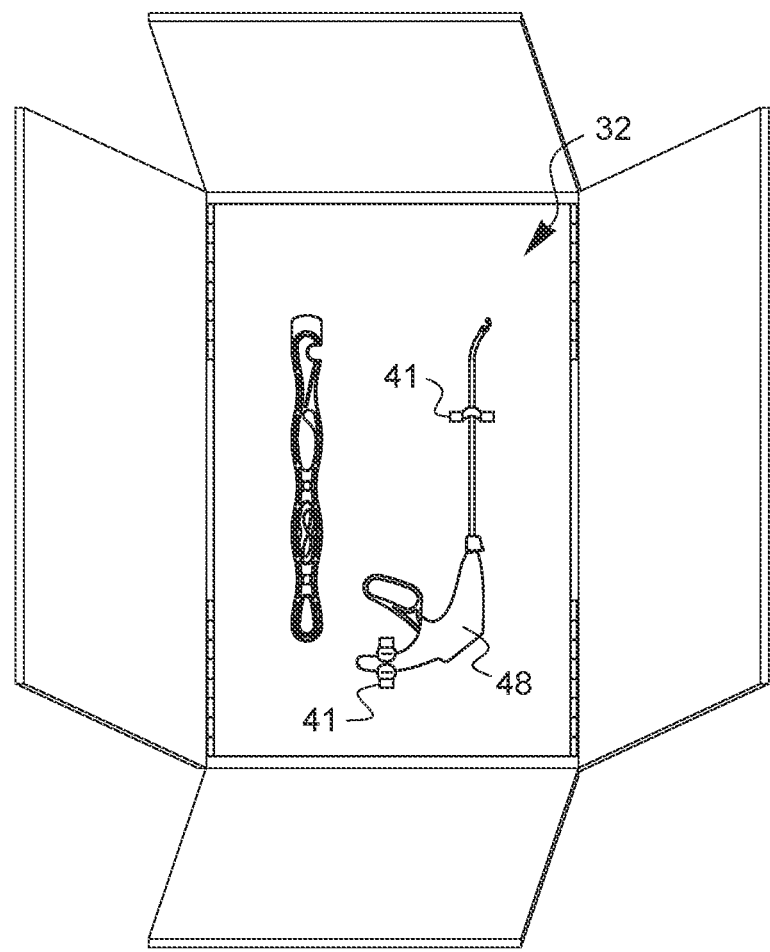
FIG. 2 is a top view of the box of FIG. 1, open and showing the top of the packed surgical procedure kit.

FIG. 2 is a top view of the box 30, where the box 30 has been opened and the top of the packed surgical procedure kit 32 may be seen. Although not shown here, the surgical procedure kit 32 may be further packaged within a tray that is sealed with a barrier layer, such as a Tyvek® layer, polypropylene-polyethylene film, paper and the like. Such a tray and barrier layer would be useful to ensure that a sterilized surgical procedure kit 32 stays sterile until such barrier layer is opened at the time of surgical use. In other embodiments, the surgical procedure kit 32 may not include a tray, but may be wrapped in a barrier layer.

Figure 3:
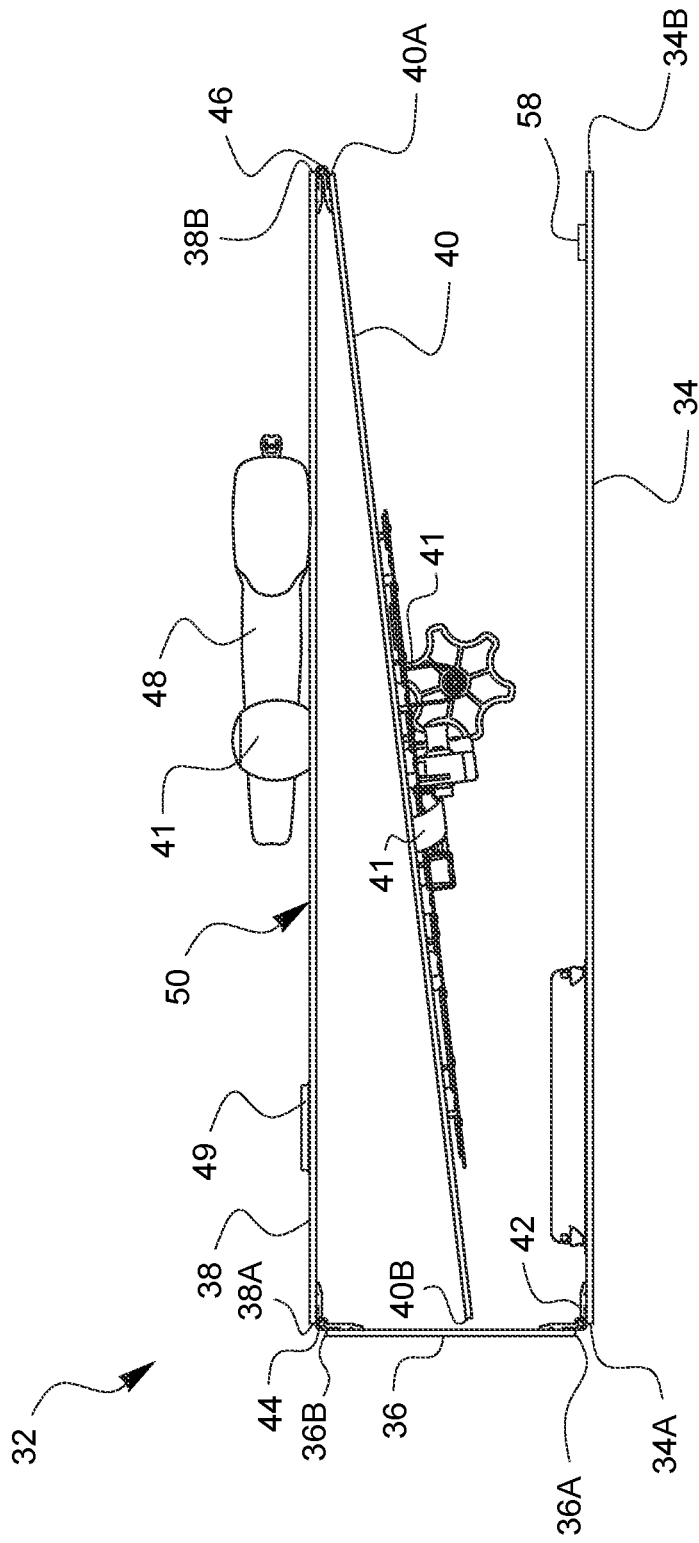
FIG. 3 is a side view of the surgical procedure kit after it has been removed from the box of FIGS. 1 and 2.

FIG. 3 shows a side view of the surgical procedure kit 32 after it has been removed from the box 30. In FIG. 3, the surgical procedure kit 32 is still in a packed configuration. The position illustrated in FIG. 3 may be referred to as a packed state or position, or as a shipping state or shipping position for the surgical procedure kit 32. The kit 32 has a base 34, an expansion panel 36, a first tent panel 38, and a second tent panel 40. One or more first hinges 42 pivotably couple a first edge 34A of the base 34 to a first edge 36A of the expansion panel 36. One or more second hinges 44 pivotably couple the second edge 36B of the expansion panel 36 to a first edge 38A of the first tent panel 38. One or more third hinges 46 pivotably couple a second edge 38B of the first tent panel 38 to a first edge 40A of the second tent panel 40.

In the packed configuration of FIG. 3, some surgical devices 48 may be accessible on an outward side 50 of the first tent panel 38. Although not necessary, in some embodiments, the surgical devices on the outward side 50 of the first tent panel 38 may correspond to those needed for initial stages of an associated minimally invasive surgical procedure. This may be advantageous because such instruments may be accessed even before further setup of the surgical procedure kit 32 takes place. In such a situation, however, not all of the surgical devices 48 on the outward side 50 of the first tent panel 38 need to be for initial stages of the procedure, and in some embodiments, none of the instruments in this location would be for initial stages of the procedure.

FIG. 4 is a side view showing an intermediate deployment position of the surgical procedure kit of FIG. 3. The first and second tent panels 38, 40 may be rotated 52 away from the base 34, causing the expansion panel 36 to pivot on the one or more first hinges 42 so that the expansion panel 36 lies in substantially the same plane as the base 34.

Figure 5A:
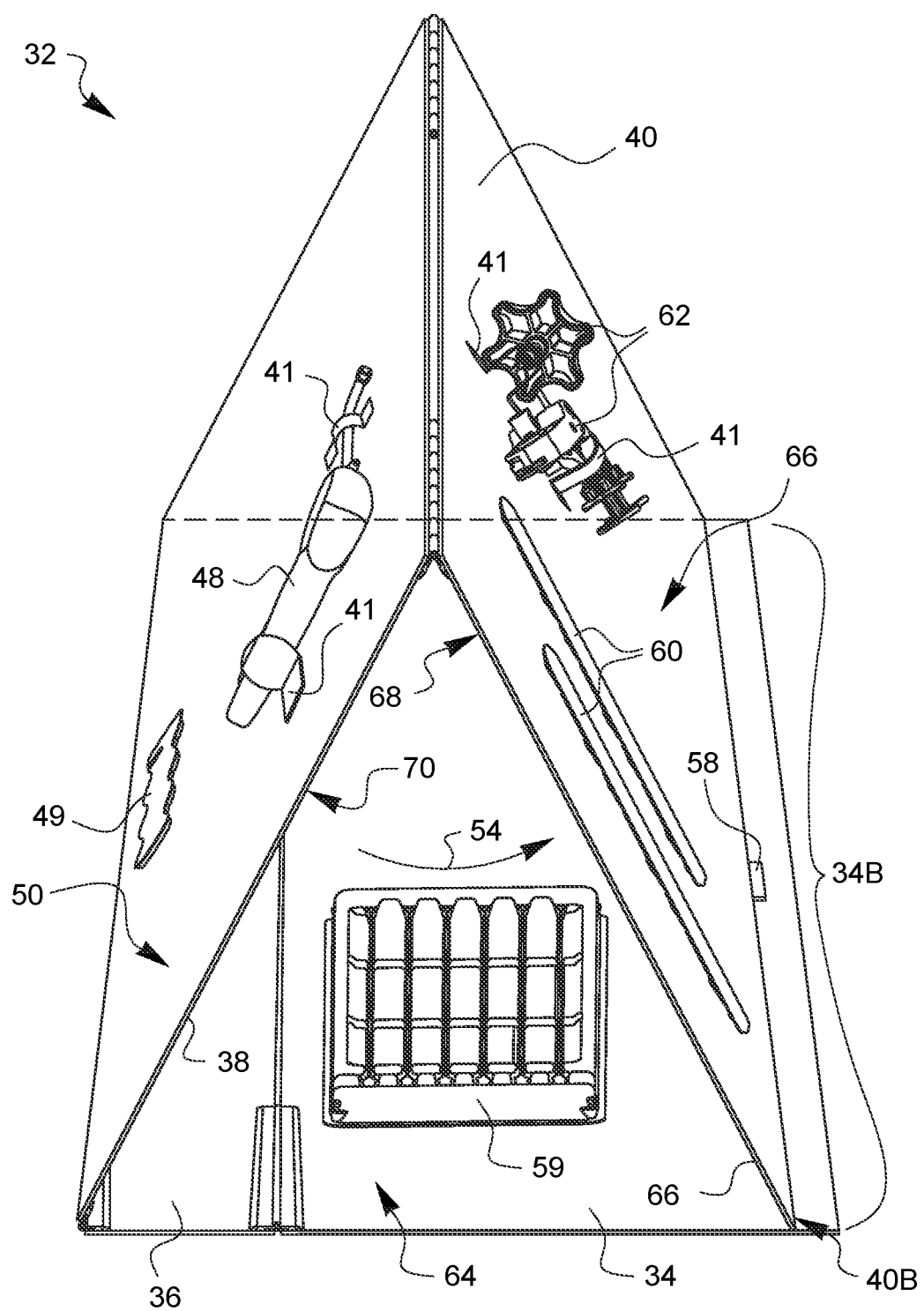
FIG. 5A is a perspective view of the surgical procedure kit of FIG. 3 in a fully deployed state.

As shown in FIG. 5A, the second tent panel 40 may be rotated 54 and moved so that a second edge 40B of the second tent panel 40 engages one or more stops 58 on the inward facing side 64 of the base 34. In other embodiments, the base 34 may have one or more stops, or other retaining feature, in proximity to or on the second edge 34B of the base 34, configured to temporarily hold the second edge 40B of the second tent panel 40 in place when opened. When engaged as shown in FIG. 5A, the first and second tent panels 38, 40 form a tent with respect to the base panel 34. The position illustrated in FIG. 5A may be referred to as a deployed state or a deployed position for the surgical procedure kit. As shown, this embodiment has surgical devices 48, 49 mounted on an outward side 50 of the first tent panel 38, surgical device 59 mounted on an inward side 64 of the base panel 34, and surgical devices 60, 62 mounted on an outward side 66 of the second tent panel 40, respectively. Although the surgical devices 48, 49, 59, 60, and 62 could be other devices in other embodiments, in this embodiment, these devices are an automated suturing device, suture, suture management devices, snares, and a surgical retractor, respectively. In other embodiments, surgical devices could also or alternately be mounted on the inward sides 68, 70 of the tent panels 40, 38, respectively. Although not necessary, in some embodiments, the surgical devices on the outward side 66 of the second tent panel 40 may correspond to those needed for intermediate stages of the associated minimally invasive surgical procedure. This may be advantageous because as the surgical procedure kit is opened from the shipping state to the deployed stage, the instruments may be accessed as the surgical procedure kit 32 is in the process of being deployed. In some embodiments, particular surgical instruments may be attached to panels 38, 40 corresponding to a specific stage in a surgical procedure. However, not all of the surgical devices 48, 49, 59, 60, 62 need to be associated with a specific stage of a procedure and in some embodiments, none of the instruments are associated with a specific stage of a surgical procedure.

Figure 5B:
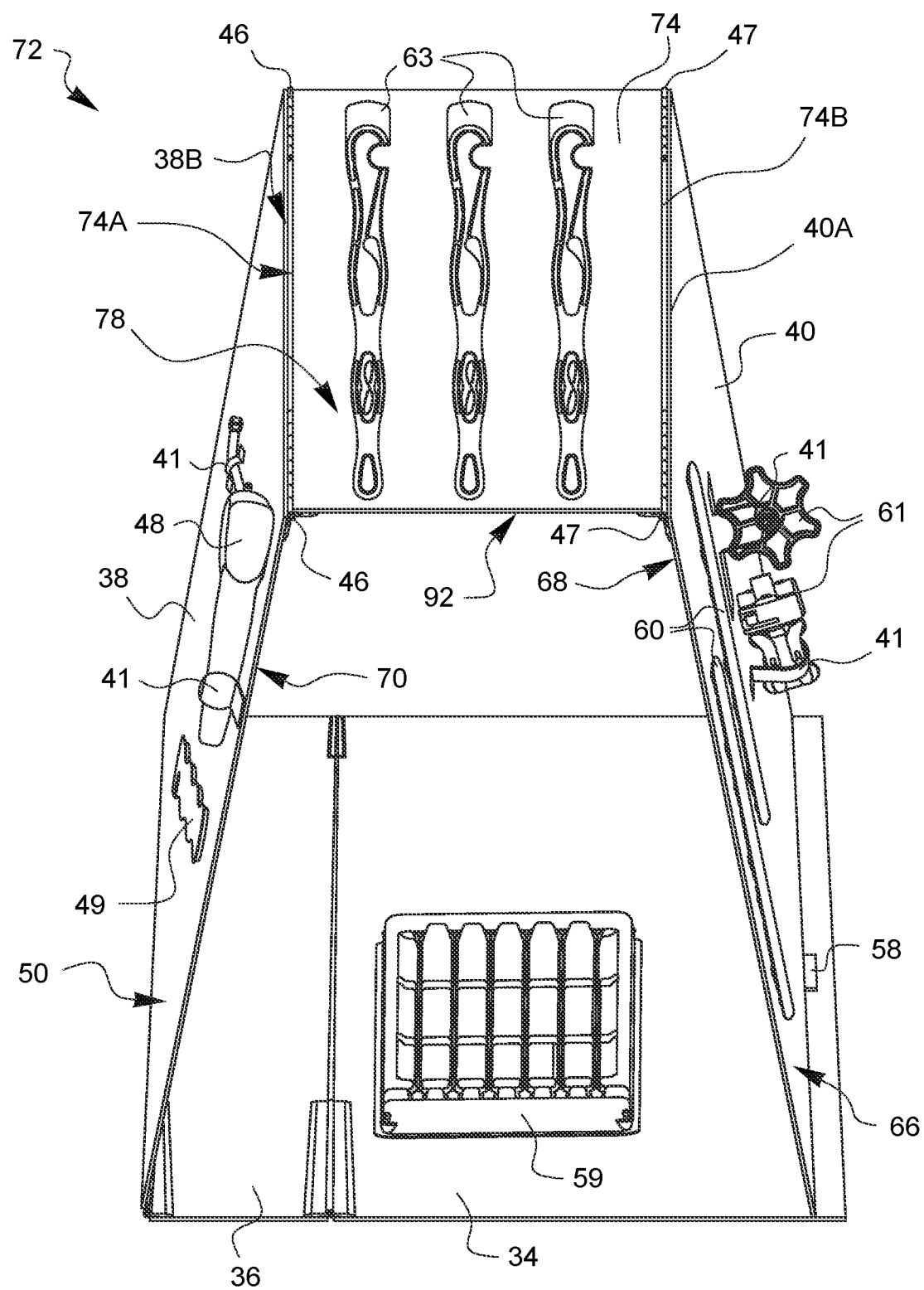
FIG. 5B is a perspective view of another embodiment of a surgical procedure kit with a second expansion panel in a fully deployed state.

FIG. 5B illustrates a different embodiment of a surgical procedure kit 72 in a deployed position. The embodiment shown in FIG. 5B is similar to the surgical procedure kit 32 shown in FIG. 5A, except the surgical procedure kit 72 in FIG. 5B includes a second expansion panel 74, located between the first and second tent panels 38, 40 to create more room for devices. One or more third hinges 46 pivotably couple a first edge 74A of the second expansion panel 74 to the second edge 38B of the first tent panel 38.

One or more fourth hinges 47 pivotably couple a second edge 74B of the second expansion panel 74 to the first edge 40A of the second tent panel 40. In this embodiment, additional surgical devices 63 are mounted on the outwards side 78 of the second expansion panel 74.

Figure 9:
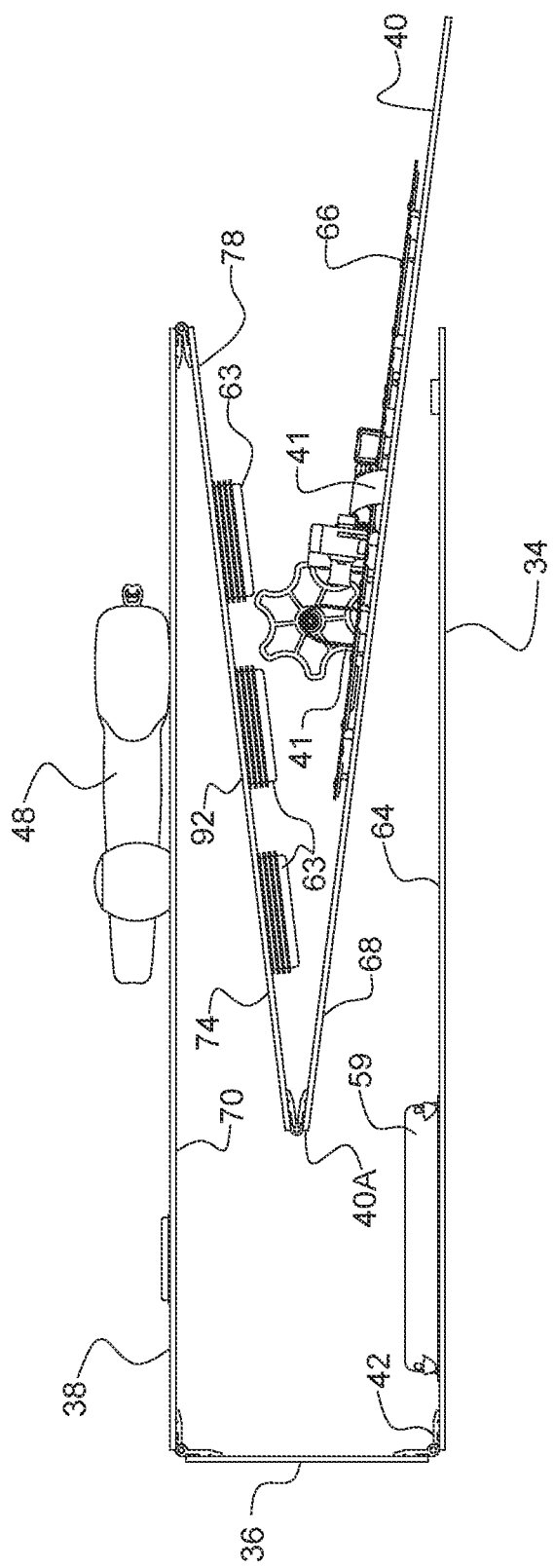
FIG. 9 is a side view of the surgical procedure kit of FIG. 5B in a packed state.

Although the deployed position for the surgical procedure kit 72 is shown in FIG. 5B, the kit 72 can start in a packed state (illustrated in FIG. 9) as follows: In the packed state, the first expansion panel 36 would be folded up at approximately a right angle to the base 34. The first tent panel 38 would be folded at approximately a right angle to the first expansion panel 36 so that the inward side 70 of the first tent panel 38 approximately faces towards the inward side of side 64 of the base 34. The second expansion panel 74 would be folded to be between the first tent panel 38 and the base 34 such that the inward side 92 of the second expansion panel 74 faces the inward side 70 of the first tent panel 38. The second tent panel 40 would be folded back so that the outward side 66 of the second tent panel 40 faces the outward side 78 of the second expansion panel 74 while the inward side 68 of the second tent panel 40 faces the inward side 64 of the base 34. One or more of the hinges could be configured to have motion limits or locks or both to help hold the deployed position of FIG. 5B since freely moving hinges with the second expansion panel 74 could result in the structure collapsing (unlike the structure of the embodiment of FIG. 5A, which is self-stabilizing).

The various hinges discussed herein could be a wide variety of types, including, but not limited to piano style hinges and living hinges of a flexible material. The base 34, expansion panel 36, first tent panel 38, second tent panel 40, and second expansion panel 74 may be made from a variety of materials, including, but not limited to plastic and cardboard. The material should be chosen to enable the tent shape of the deployed position to hold without substantial sagging that might compromise the ability of the tent to maintain its shape and/or without compromising the ability of a user to reach into the tent to access the various surgical equipment stored therein and/or thereon. In some embodiments, ribbing, corrugations, and the like may be included as part of the base 34, expansion panel 36, first tent panel 38, and/or second tent panel 40 in order to strengthen those portions of the surgical procedure kit 32. In some embodiments, one or more of the base 34, expansion panel 36, first tent panel 38, and the second tent panel 40 may have receptacles 41 mounted thereon in order to hold the devices in place until removed by the user. The shapes and configurations of the receptacles 41 will largely be determined by each surgical device, however, the orientation of the receptacle in relation to the stresses on the given panel may be chosen to provide strength to resist sagging. The receptacles can be made of a variety of materials including "hook and loop" fasteners or straps, fugitive glue, metal and plastic clips, or any other material suited for the specific surgical instrument required in a given procedure.

As shown in FIGS. 5A and 5B, the surgical procedure kits 32, 72 only take up a foot print associated with the base 34 and the expansion panel 36, while providing approximately two to four times as much instrument storage area as the base 34 alone when taking into account the real estate of the inner and outward sides of the first and second tent panels 38, 40 and second expansion panel 74. Each of these surfaces is easily accessible to the surgical team. In embodiments where the tent panels 38, 40 and the second expansion panel 74 are transparent, such as illustrated herein, the user also has the ability to see the items on the interior of the tent much better than if the tent panels 38, 40 and second expansion panel 74 were not transparent.

Figure 6:
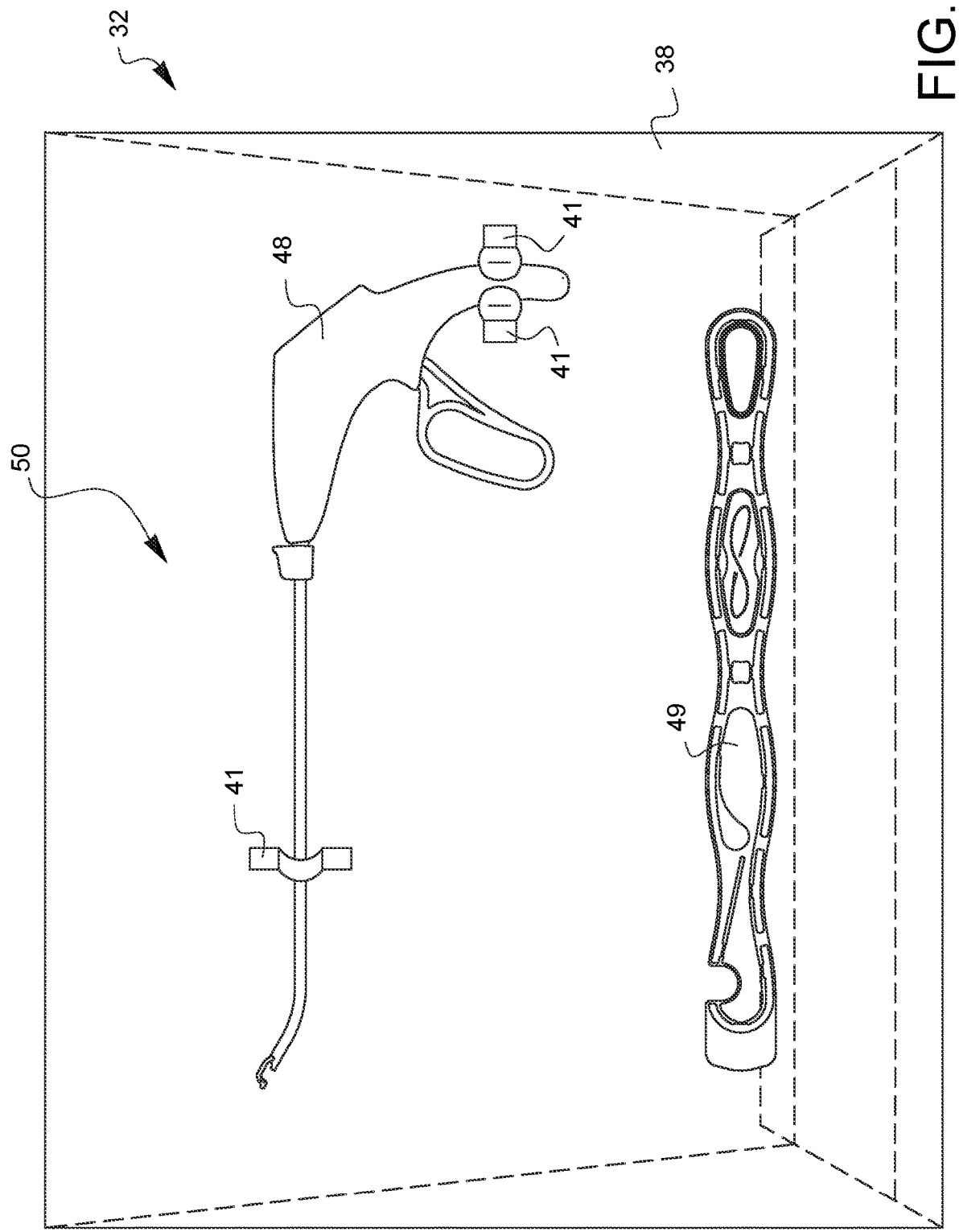
FIG. 6 is a side view of the outward side of the first tent panel of the deployed surgical procedure kit of FIG. 3.
Figure 7:
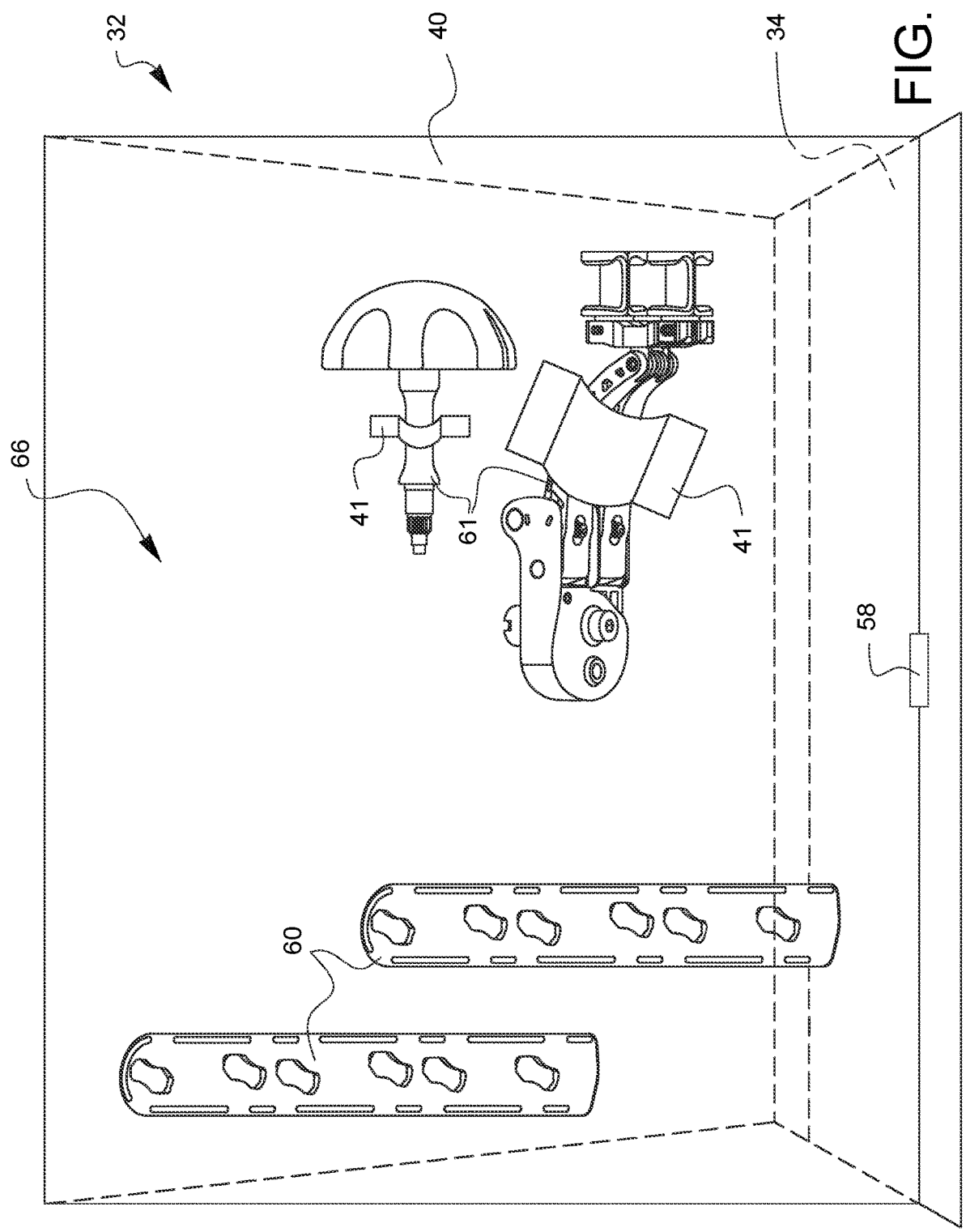
FIG. 7 is a side view of the outward side of the second tent panel of the deployed surgical procedure kit of FIG. 3.
Figure 8:
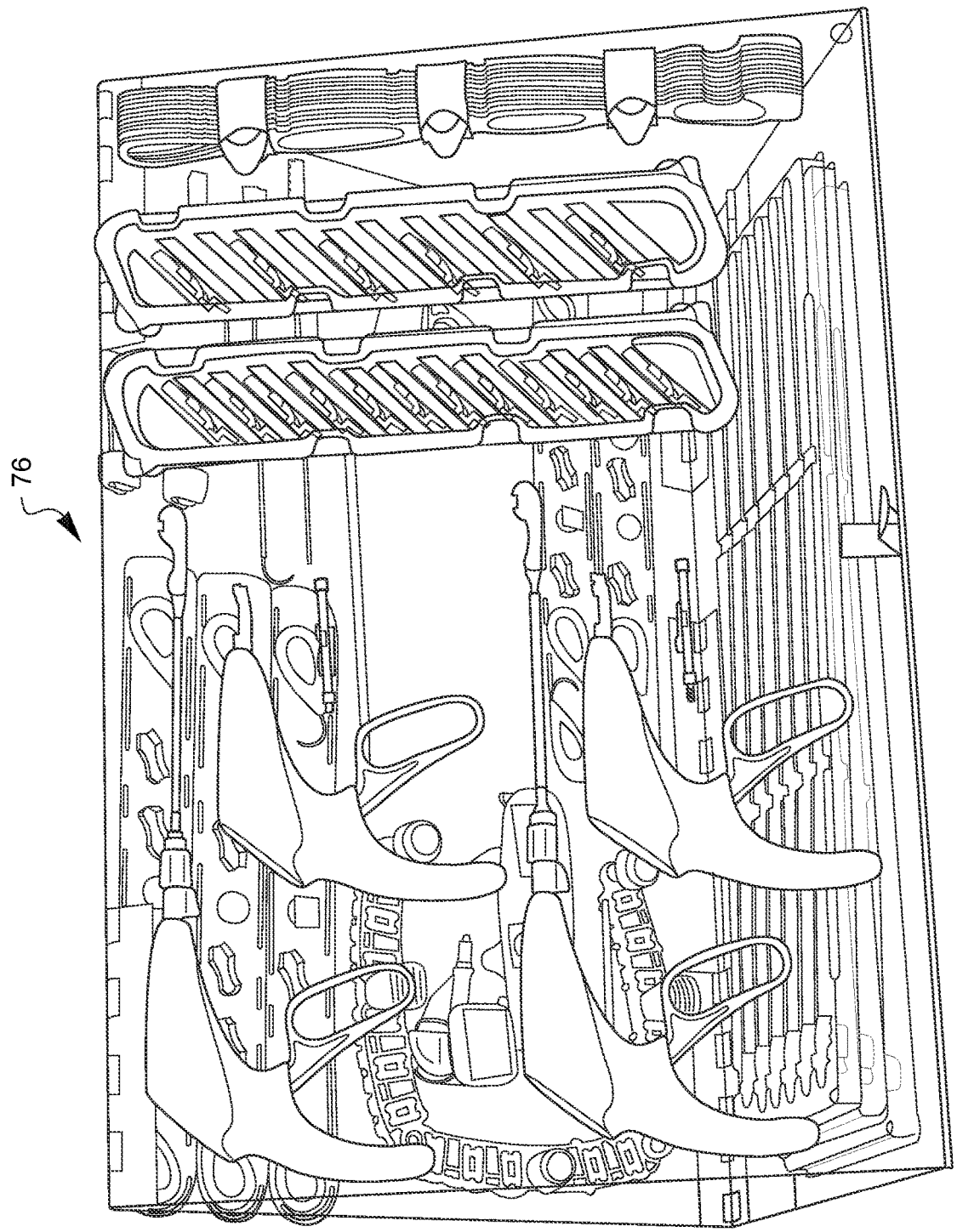
FIG. 8 is a perspective view of another embodiment of a surgical procedure kit in a deployed state.

FIG. 6 is a side view of the outward side 50 of the first tent panel 38 of the deployed surgical procedure kit 32 from FIG. 5A. FIG. 7 is a side view of the outward side 66 of the second tent panel 40 of the deployed surgical procedure kit 32 from FIG. 5A. FIG. 8 is a perspective view of another embodiment of a surgical procedure kit 76 in the deployed state. The orientation and distribution of specific surgical devices on any given embodiment will differ, and the devices illustrated are merely shown as examples of one possible selection and layout.

The advantage of the embodied surgical procedure kits lies in the reduction of packaging, ease of setup, and accessibility of the entire set of devices at once without having to dig through packing layers and without having to use multiple surgical tables.

Various advantages of a surgical procedure kit have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical procedure kit, comprising:
   a base having a first edge and a second edge, the base comprising at least one base receptacle configured to releasably hold a first surgical device;
   a first expansion panel having a first edge and a second edge, wherein the first edge of the first expansion panel is pivotably coupled to the first edge of the base;
   a first tent panel having a first edge and a second edge, wherein the first edge of the first tent panel is pivotably coupled to the second edge of the first expansion panel, the first tent panel comprising at least one first tent panel receptacle configured to releasably hold a second surgical device;
   a second expansion panel having a first edge and a second edge, wherein the first edge of the second expansion panel is pivotably coupled to the second edge of the first tent panel; and
   a second tent panel having a first edge and a second edge, wherein the first edge of the second tent panel is pivotably coupled to the second edge of the second expansion panel, the second tent panel comprising at least one second tent panel receptacle configured to releasably hold a third surgical device; and
   wherein:
   the base further comprises one or more stops on an inward side of the base in proximity to the second edge of the base, the one or more stops configured to receive the second edge of the second tent panel;
   wherein the base, the first expansion panel, the first tent panel, the second expansion panel and the second tent panel are configurable between a deployed state and a shipping state, wherein in the shipping state the first expansion panel is at substantially a right angle to the base and the first tent panel is at substantially a right angle to the first expansion panel such that an inward side of the first tent panel substantially faces the base, and wherein each of the base, the first expansion panel, the first tent panel, the second expansion panel and the second tent panel are spaced from one another in the shipping state allowing for the first surgical device and the third surgical device to be maintained between the base and the second expansion panel.

2. The surgical procedure kit of claim 1, wherein the first expansion panel comprises at least one first expansion panel receptacle configured to releasably hold at least one fourth surgical device.

3. The surgical procedure kit of claim 1, wherein the second expansion panel includes at least one second expansion panel receptacle configured to releasably hold a fifth surgical device.

4. The surgical procedure kit of claim 3, wherein the first tent panel receptacle is disposed on the outward side of the first tent panel.

5. The surgical procedure kit of claim 1, wherein the at least one second tent panel receptacle is located on an outward side of the second tent panel.

6. The surgical procedure kit of claim 1, wherein (a) the first edge of the first expansion panel is pivotably coupled to the first edge of the base by one or more first hinges, (b) the first edge of the first tent panel is pivotably coupled to the second edge of the first expansion panel by one or more second hinges, (c) the first edge of the second expansion panel is pivotably coupled to a second edge of the first tent panel by one or more third hinges, and (d) the first edge of the second tent panel is pivotably coupled to the second edge of the second expansion panel by one or more fourth hinges.

7. The surgical procedure kit of claim 1, wherein in the shipping state, the second expansion panel is disposed between the first tent panel and the base.

8. The surgical procedure kit of claim 7, wherein in the shipping state, an inward side of the second expansion panel faces the inward side of the first tent panel.

9. The surgical procedure kit of claim 8, wherein in the shipping state, the second tent panel is disposed between the second expansion panel and the base.

10. The surgical procedure kit of claim 9, wherein in the shipping state, an outward side of the second tent panel faces an outward side of the second expansion panel.

11. The surgical procedure kit of claim 1, wherein in the deployed state, the first expansion panel lies in substantially the same plane as the base.

12. The surgical procedure kit of claim 10, wherein in the deployed state, the second expansion panel lies in a plane that is offset from and substantially parallel to a plane defined by the base.

13. The surgical procedure kit of claim 1, wherein the at least one first tent panel receptacle is disposed on an outward side of the first tent panel.

14. A surgical procedure kit, comprising:
    a base having a first edge and a second edge, the base comprising at least one base receptacle configured to releasably hold a first surgical device;
    a first expansion panel having a first edge and a second edge wherein the first edge of the first expansion panel is pivotably coupled to the first edge of the base;
    a first tent panel having a first edge and a second edge wherein the first edge of the first tent panel is pivotably coupled to the second edge of the first expansion panel, the first tent panel comprising at least one first tent panel receptacle configured to releasably hold a second surgical device;

a second expansion panel having a first edge and a second edge, wherein the first edge of the second expansion panel is pivotably coupled to the second edge of the first tent panel; and a second tent panel having a first edge and a second edge wherein the first edge of the second tent panel is pivotably coupled to the second edge of the second expansion panel, the second tent panel comprising at least one second tent panel receptacle configured to releasably hold a third surgical device, wherein the base, the first expansion panel, the first tent panel, the second expansion panel, and the second tent panel are configurable between a deployed state and a shipping state, wherein in the deployed state, the second edge of the second tent panel is configured to be coupled to a portion of an inward side of the base, and wherein in the shipping state: (a) the first expansion panel is at substantially a right angle to the base and the first tent panel is at substantially a right angle to the first expansion panel such that an inward side of the first tent panel substantially faces the inward side of the base, (b) the second expansion panel is disposed between the first tent panel and the base, and (c) at least a portion of the second tent panel is disposed between the second expansion panel and the base.

15. The surgical procedure kit of claim 14, wherein the first tent panel receptacle is disposed on the outward side of the first tent panel and the at least one second tent panel receptacle is located on an outward side of the second tent panel.

16. The surgical procedure kit of claim 14, wherein in the shipping state, an inward side of the second expansion panel faces the inward side of the first tent panel.

17. The surgical procedure kit of claim 14, wherein in the shipping state, an outward side of the second tent panel faces an outward side of the second expansion panel.

18. The surgical procedure kit of claim 14, wherein in the deployed state, the first expansion panel lies in substantially the same plane as the base and in the deployed state, the second expansion panel lies in a plane that is offset from and substantially parallel to a plane defined by the base.

19. The surgical procedure kit of claim 14, wherein the base further comprises one or more stops on the inward side of the base in proximity to the second edge of the base, the one or more stops configured to receive the second edge of the second tent panel to couple the second edge of the tent panel to the portion of the inward side of the base.

20. The surgical procedure kit of claim 14, wherein each of the base, the first expansion panel, the first tent panel, the second expansion panel and the second tent panel are spaced from one another in the shipping state allowing for the first surgical device and the third surgical device to be maintained between the base and the second tent panel.

\* \* \* \* \*